(12) United States Patent
Tobinick

(10) Patent No.: US 6,982,089 B2
(45) Date of Patent: *Jan. 3, 2006

(54) CYTOKINE ANTAGONISTS FOR NEUROLOGICAL AND NEUROPSYCHIATRIC DISORDERS

(75) Inventor: Edward Lewis Tobinick, Los Angeles, CA (US)

(73) Assignee: TACT IP, LLC, Highland Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/269,745

(22) Filed: Oct. 9, 2002

(65) Prior Publication Data

US 2003/0049256 A1 Mar. 13, 2003

Related U.S. Application Data

(63) Continuation-in-part of application No. 10/236,097, filed on Sep. 6, 2002, now abandoned, which is a continuation-in-part of application No. 09/841,844, filed on Apr. 25, 2001, now Pat. No. 6,537,549, which is a continuation-in-part of application No. 09/826,976, filed on Apr. 5, 2001, now Pat. No. 6,419,944, which is a continuation-in-part of application No. 09/563,651, filed on May 2, 2000, now Pat. No. 6,471,961, which is a continuation-in-part of application No. 09/476,643, filed on Dec. 31, 1999, now Pat. No. 6,177,077, which is a continuation-in-part of application No. 09/275,070, filed on Mar. 23, 1999, now Pat. No. 6,015,557, which is a continuation-in-part of application No. 09/256,388, filed on Feb. 24, 1999, now abandoned.

(51) Int. Cl.
*A61K 9/00* (2006.01)
*A61K 39/40* (2006.01)

(52) U.S. Cl. ............... 424/400; 424/422; 424/427; 424/434; 424/134.1; 514/885; 514/886

(58) Field of Classification Search ......... 424/422, 424/400, 427, 434, 134.1; 514/885, 898, 514/362, 363, 364
See application file for complete search history.

(56) References Cited

U.S. PATENT DOCUMENTS

| | | | |
|---|---|---|---|
| 5,075,222 A | 12/1991 | Hannum et al. | |
| 5,574,022 A | 11/1996 | Roberts et al. | |
| 5,605,690 A | 2/1997 | Jacobs et al. | |
| 5,756,482 A | 5/1998 | Roberts et al. | |
| 5,863,769 A | 1/1999 | Young | |
| 6,013,253 A | 1/2000 | Martin et al. | |
| 6,015,557 A | 1/2000 | Tobinick et al. | 424/134.1 |
| 6,096,728 A | 8/2000 | Collins et al. | |
| 6,159,460 A | 12/2000 | Thompson et al. | |
| 6,177,077 B1 | 1/2001 | Tobinick | 424/134.1 |
| 6,277,969 B1 | 8/2001 | Le et al. | |
| 6,406,867 B1 | 6/2002 | Yu et al. | 435/7.2 |
| 6,419,934 B1 | 7/2002 | Tobinick | 424/400 |
| 6,419,944 B2 | 7/2002 | Tobinick | 424/422 |
| 6,423,321 B2 | 7/2002 | Tobinick | 424/400 |
| 6,428,787 B1 | 8/2002 | Tobinick | 424/134.1 |
| 6,471,961 B1 | 10/2002 | Tobinick | 424/134.1 |
| 6,537,549 B2 | 3/2003 | Tobinick | 424/134.1 |

OTHER PUBLICATIONS

Kroin et al. The distribution of medication along the spinal canal after chronic intrathecal administration. Neurosurgery, 1993, vol. 33(2), 226–230.*

* cited by examiner

*Primary Examiner*—Thurman K. Page
*Assistant Examiner*—Lakshmi Channavajjala
(74) *Attorney, Agent, or Firm*—Ezra Sutton, Esq.

(57) ABSTRACT

Methods for treating neurological or neuropsychiatric diseases or disorders in humans by administering to the human a therapeutically effective dose of specific biologics are presented. The biologics of consideration include antagonists of tumor necrosis factor or of interleukin-1. The administration of these biologics is performed by specific methods, most, but not all of which fall into the category of anatomically localized administration designed for perispinal use. Anatomically localized administration involving perispinal use includes, but is not limited to the subcutaneous, intramuscular, interspinous, epidural, peridural, parenteral or intrathecal routes. Additonally, intranasal administration is discussed as a method to provide therapeutic benefit. The clinical conditions of consideration include, but are not limited to the following: diseases of the brain, including neurodegenerative diseases such as Alzheimer's Disease and Parkinson's Disease; migraine headache; spinal radiculopathy associated with intervertebral disc herniation, post-herpetic neuralgia, reflex sympathethic dystrophy, neuropathic pain, vertebral disc disease, low back pain, amyotrophic lateral sclerosis, chronic fatigue syndrome; and neuropsychiatric diseases, including bipolar affective disorder, anorexia nervosa, nicotine withdrawal, narcotic addiction, alcohol withdrawl, postpartum depression, and schizoaffective illness.

15 Claims, No Drawings

CYTOKINE ANTAGONISTS FOR NEUROLOGICAL AND NEUROPSYCHIATRIC DISORDERS

RELATED APPLICATIONS

This is a continuation-in-part of application Ser. No. 10/236,097, filed on Sep. 6, 2002 now abandoned, which is a continuation-in-part of application Ser. No. 09/841,844, filed on Apr. 25, 2001 Now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/563,651, filed on May 2, 2000 Now U.S. Pat. No. 6,471,961, which is a continuation-in-part of application Ser. No. 09/476,643, filed on Dec. 31, 1999, now U.S. Pat. No. 6,177,077, which is a continuation-in-part of application Ser. No. 09/275,070, filed on Mar. 23, 1999, now U.S. Pat. No. 6,015,557, which is a continuation-in-part of application Ser. No. 09/256,388, filed on Feb. 24, 1999, now abandoned.

FIELD OF THE INVENTION

The present invention relates to novel methods of use of specific cytokine antagonists for the treatment of neuropsychiatric and neurological disorders in humans. More particularly, these cytokine antagonists are used in a new treatment of neuropsychiatric and neurologic diseases and disorders, including, but not limited to affective disorders, including unipolar and bipolar affective disorders; schizoaffective illness, schizophrenia, autism, depression, anorexia nervosa, obsessive-compulsive disorders, narcotic addiction, and smoking cessation/nicotine withdrawal; diseases and disorders of the brain; neurodegenerative disorders, including but not limited to Parkinson's Disease and Alzheimer's Disease; spinal cord injury, amyotrophic lateral sclerosis; headache syndromes, including, but not limited to migraine headaches and cluster headaches; neurologic disorders associated with neuropathic pain, including, but not limited to lumbar and cervical radiculopathy, low back pain, vertebral disc disease, fibromyalgia, post-herpetic neuralgia, and reflex sympathetic dystrophy; and chronic fatigue syndrome; utilizing specific anatomic methods of administration of these specific biologics. The delivery of these cytokine antagonists is performed by specific methods, most of which fall into the categories of perispinal administration or intranasal administration. Perispinal administration involves an anatomically localized injection performed so as to deliver the therapeutic molecule directly into the vicinity of the spine. Perispinal administration includes, but is not limited to the subcutaneous, intramuscular, interspinous, epidural, peridural, parenteral, or intrathecal routes, and may be perilesional or alternatively, particularly when treating diseases of the brain, remote from the ultimate site of pathology. Intranasal administration includes the delivery of these particular cytokine antagonists by instillation into the nasal passages, either by nasal spray or nasal inhaler. The cytokine antagonists of consideration are those designed to block the action of, inhibit, or antagonize the biologic effects of tumor necrosis factor-alpha (TNF) or interleukin-1 (IL-1). These antagonists may take the form of a fusion protein (such as etanercept); a monoclonal antibody (such as infliximab); a binding protein (such as onercept; Serono); an antibody fragment (such as CDP 870, Pharmacia); or other types of molecules which are potent, selective, and specific inhibitors of the action of these pro-inflammatory cytokines and are capable of being used by parenteral injection.

BACKGROUND OF THE INVENTION

Localized administration for the treatment of localized clinical disorders has many clinical advantages over the use of conventional systemic treatment. Locally administered medication after delivery diffuses through local capillary, venous, arterial, and lymphatic action to reach the anatomic site of pathology, or, alternatively, to reach the cerebrospinal fluid (CSF). In addition local administration of a biologic in the vicinity of the spine (perispinal administration) has the key advantage of improved delivery of the agent to the central nervous system (CNS). Local intranasal administration of a biologic is another method to improve delivery of the biologic to the CNS, and is discussed here as a method to treat neuropsychiatric disorders, including disorders of mood (depression, bipolar disorder) utilizing TNF antagonists or IL-1 antagonists.

All of the cytokine antagonists which are currently available have been developed for systemic administration. This is because all were developed to treat systemic illnesses, including rheumatoid arthritis, juvenile rheumatoid arthritis, psoriatic arthritis, or Crohn's Disease.

The use of cytokine antagonists to treat neurological disorders is discussed in several previous patents of this inventor, including U.S. Pat. Nos. 6,015,557, 6,177,077, 6,419,944 B2 and other pending applications of this inventor. This invention includes further applications of these ideas.

Perispinal administration of biologics when compared to systemic administration, carries with it one or more of the following advantages:

1) greater efficacy due to the achievement of higher local concentration;
2) greater efficacy due to the ability of the administered therapeutic molecule to reach the target tissue without degradation caused by hepatic or systemic circulation;
3) more rapid onset of action;
4) longer duration of action;
5) Potentially fewer side effects, due to lower required dosage;
6) greatly improved efficacy due to improved delivery of the therapeutic molecule to the CNS.

Clinical experience utilizing perispinal administration of etanercept for treating lumbar and cervical radiculopathy and other forms of neuropathic pain caused by vertebral disc disease has demonstrated the dramatic efficacy, and the extraordinarily rapid onset of action produced by perispinal administration of etanercept for these disorders. Perispinal administration of the other cytokine antagonists of consideration here, for treating other neurological disorders or for treating neuropsychiatric disorders, as partially enumerated above, shares the above advantages.

The therapeutic molecules of consideration here have many biologic effects. Etanercept, for example, in addition to being a potent anti-inflammatory also has important anti-apoptotic effects which may be of particular importance in treating neurodegenerative diseases, such as Alzheimer's Disease and Parkinson's Disease, where apoptosis plays a pathogenetic role.

Biologics have been developed which have been shown to offer dramatic clinical benefit for systemic illnesses in humans, even for those disorders which have not responded to large and repeated doses of corticosteroids. These biologics fall into the category of cytokine antagonists because they block, or antagonize, the biologic action of a specific cytokine which has adverse clinical effects. These cytokines include the pro-inflammatory cytokines interleukin-1 and TNF. For the purposes of this discussion, "antagonist", "inhibitor", and "blocker" are used interchangeably.

Specific inhibitors of TNF, only recently commercially available, now provide for therapeutic intervention in TNF mediated disorders. These agents have been developed to treat systemic illnesses, and therefore have been developed for systemic administration. Various biopharmaceutical companies have developed TNF antagonists to treat systemic illnesses: Immunex Corporation developed etanercept (Enbrel) to treat rheumatoid arthritis; Johnson and Johnson developed infliximab (Remicade) to treat Crohn's Disease and rheumatoid arthritis; D2E7, a human anti-TNF monoclonal antibody (Abbott) is being developed to treat rheumatoid arthritis and Crohn's Disease; Celltech is developing CDP 571 to treat Crohn's Disease and CDP 870 to treat rheumatoid arthritis; and Serono is developing onercept, a recombinant TNF binding protein (r-TBP-1) for treating rheumatoid arthritis and psoriasis/psoriatic arthritis.

Recent research has demonstrated that a new TNF antagonist can be manufactured from an existing molecule by subtracting a portion of the amino acid sequence from the molecule. This has the advantage of making the molecule smaller. This smaller molecule can be easier to manufacture and may have clinical advantages, such as reduced immunogenicity in the human in vivo. Therefore, the molecules of consideration here shall also include, in addition to those specified, any molecule which contains a fragment of any of the named molecules. A fragment shall be defined as an identical amino acid sequence 50% or greater in length of the original molecule and possessing TNF binding capability or interleukin-1 binding capability.

DESCRIPTION OF THE PRIOR ART

Pharmacologic chemical substances, compounds and agents which are used for the treatment of neurological disorders, trauma, injuries and compression having various organic structures and metabolic functions have been disclosed in the prior art. For example, U.S. Pat. Nos. 5,756,482 and 5,574,022 to ROBERTS et al disclose methods of attenuating physical damage to the nervous system and to the spinal cord after injury using steroid hormones or steroid precursors such as pregnenolone, and pregnenolone sulfate in conjunction with a non-steroidal anti-inflammatory substance such as indomethacin. These prior art patents do not teach the use of specific cytokine antagonists administered by the perispinal route as a way of treating neurological or neuropsychiatric disorders or diseases., as in the present invention.

U.S. Pat. No. 5,863,769 discloses using IL-1 RA for treating various diseases. However, it does not disclose administering cytokine antagonists by the perispinal route as a way of treating neurological or neuropsychiatric disorders or diseases.

U.S. Pat. No. 6,013,253 discloses using interferon and IL-1 RA for treating multiple sclerosis. However, it does not disclose administering cytokine antagonists by the perispinal route as a way of treating neurological or neuropsychiatric disorders or diseases.

U.S. Pat. No. 5,075,222 discloses the use of IL-1 inhibitors for treatment of various disorders. However, it does not disclose administering cytokine antagonists by the perispinal route as a way of treating neurological or neuropsychiatric disorders or diseases.

U.S. Pat. No. 6,159,460 discloses the use of IL-1 inhibitors for treatment of various disorders. However, it does not disclose administering cytokine antagonists by the perispinal route as a way of treating neurological or neuropsychiatric disorders or diseases.

U.S. Pat. No. 6,096,728 discloses the use of IL-1 inhibitors for treatment of various disorders. However, it does not disclose administering cytokine antagonists by the perispinal route as a way of treating neurological or neuropsychiatric disorders or diseases.

U.S. Pat. No. 6,277,969 discloses the use of anti-TNF antibodies for treatment of various disorders. However, it does not disclose administering cytokine antagonists by the perispinal route as a way of treating neurological or neuropsychiatric disorders or diseases.

U.S. Pat. No. 5,605,690 discloses the use of TNF inhibitors for treatment of various disorders. However, it does not disclose administering cytokine antagonists by the perispinal route as a way of treating neurological or neuropsychiatric disorders or diseases.

None of the prior art patents disclose or teach the use of localized administration of a cytokine antagonist as in the present invention as a way of treating neurological or neuropsychiatric disorders or diseases, in which the cytokine antagonist provides the patient with a better opportunity to heal, slows disease progression, or otherwise improves the patient's health.

Accordingly, it is an object of the present invention to provide a biologic administered through perispinal administration as a new method of pharmacologic treatment of neurological or neuropsychiatric diseases or disorders such that the use of these biologics will result in the amelioration of these conditions.

Another object of the present invention is to provide cytokine antagonists for providing suppression and inhibition of the action of specific cytokines in a human to treat neurological or neuropsychiatric diseases or disorders.

Another object of the present invention is to provide cytokine antagonists that produce biologic effects in patients with neurological or neuropsychiatric diseases or disorders by inhibiting the action of specific cytokines in the human body for the immediate, short term (acute conditions) and long term (chronic conditions), such that these biologic effects will produce clinical improvement in the patient and will give the patient a better opportunity to heal, improve cognitive function, slow disease progression, prevent neurological damage, reduce pain, or otherwise improve the patient's health.

Another object of the present invention is to provide cytokine antagonists, using anatomically localized administration in the vicinity of the spine as the preferred forms of administration, that provide therapeutic benefit utilizing either acute or chronic treatment regimens for treating neurological or neuropsychiatric diseases or disorders.

SUMMARY OF THE INVENTION

The present invention provides methods for treating neurological or neuropsychiatric diseases or disorders in humans by administering to the human a therapeutically effective dose of a specific biologic. The biologics of consideration include antagonists of tumor necrosis factor-alpha or of interleukin-1. The administration of these biologics is performed by specific methods, most, but not all of which fall into the categories of anatomically localized administration involving perispinal or intranasal delivery. Anatomically localized administration involving perispinal use includes, but is not limited to the subcutaneous, intramuscular, interspinous, epidural, peridural, parenteral or intrathecal routes.

DETAILED DESCRIPTION OF THE PREFERRED EMBODIMENTS

Perispinal administration is a novel new concept for a delivery method for cytokine antagonists for treating neurological or neuropsychiatric diseases.

For the purposes of this discussion, "perispinal" means in the anatomic vicinity of the spine. For this discussion "anatomic vicinity" is generally defined as within 10 centimeters, or functionally defined as in close enough anatomic proximity to allow the therapeutic molecules of consideration herein to reach the spine and/or the subarachnoid space surrounding the spinal cord in therapeutic concentration when administered directly to this area. For the treatment of brain disorders, such as Alzheimer's, perispinal administration is effective because it delivers the biologic to the CNS in a therapeutic amount. This is accomplished through enhanced delivery of the therapeutic molecule to the CNS, either by direct diffusion or via enhanced delivery into the cerebrospinal fluid (CSF) which is present in the thecal sac. This usually occurs without direct intrathecal injection, but rather by diffusion from the peridural space into the subarachnoid space. Direct injection of these specific cytokine antagonists into the CSF (intrathecal administration) is also a form of localized anatomic administration and can be accomplished by the perispinal route.

One of the advantages of perispinal delivery is that administration is simplified. For example, administration for the treatment of an annular tear of an intervertebral disc in the lumbar spine is effective by the interspinous route adjacent to the involved disc. This route is simple and safe. Hemorrhage due to the use of long or large bore needles is minimized because perispinal administration, by the subcutaneous route, requires only a short, narrow bore needle. Time-consuming and difficult epidural injection is not necessary. Epidural administration, for the purposes of this patent, is also a form of perispinal administration, and, in certain clinical circumstances may be the delivery method of choice, despite its greater difficulty and greater risk. Local perispinal administration also has the advantage of providing a depot of therapeutic medication in the surrounding tissue, which will provide therapeutic levels of medication to the treatment site for a prolonged period of time. This decreases the necessity for another injection of medication. Additionally, administering medication locally limits the exposure of the medication to the systemic circulation, thereby decreasing renal and hepatic elimination of the medication, and decreasing exposure of the medication to systemic metabolism. All of these factors tend to increase the therapeutic half-life of the administered cytokine antagonist. Intranasal administration is also a form of localized anatomic administration. It shares the above advantages with perispinal administration, and has the additional advantage of delivering the biologic to the area (upper nasal passages) directly adjacent to the brain. Additionally the biologics are delivered in this same manner directly to branches of the olfactory nerve, providing another route of delivery to the CNS. Taken together, all of these forms of localized anatomic administration have significant clinical advantages over the various forms of systemic administration previously used to deliver these cytokine antagonists. These forms of systemic administration include the intravenous route; the intramuscular route, when the site of intramuscular administration is remote from the site of pathology; the subcutaneous route, when the site of subcutaneous administration is remote from the site of pathology (such as an abdominal, thigh, or arm administration for the treatment of sciatica); or other methods of administration which rely on the use of the systemic circulation to deliver the medication to the target area of pathology.

For the sake of this invention, the following definitions also apply: perilesional is defined as in anatomic proximity to the site of the pathologic process being treated; and peridural is defined as in anatomic proximity to the dura of the spinal cord. The "interspinous route" for the purposes of this patent, is defined as parenteral injection through the skin in the midline, in the interspace between two spinous processes, to deliver the therapeutic molecule in anatomic proximity to the spine.

Biologics to be used for the purposes of this patent fall into the general categories of TNF antagonists or interleukin-1 antagonists.

TNF antagonists include, but are not limited to the following: etanercept (Enbrel®—Amgen); infliximab (Remicade®—Johnson and Johnson); D2E7, a human anti-TNF monoclonal antibody (Knoll Pharmaceuticals, Abbott Laboratories); CDP 571 (a humanized anti-TNF IgG4 antibody); CDP 870 (an anti-TNF alpha humanized monoclonal antibody fragment), both from Celltech; soluble TNF receptor Type I (Amgen); pegylated soluble TNF receptor Type I (PEGs TNF-R1) (Amgen); and onercept, a recombinant TNF binding protein (r-TBP-1) (Serono). Antagonists of interleukin-1 include, but are not limited to Kineret® (recombinant IL1-RA, Amgen), IL1-Receptor Type 2 (Amgen) and IL-1 Trap (Regeneron).

In one preferred embodiment a patient with bipolar affective disorder complaining of severe depression is treated by injection of a TNF antagonist selected from the group of etanercept, infliximab, CDP 870, D2E7, or onercept in a therapeutically effective dose to the anatomic area adjacent to the spine.

In one preferred embodiment a patient with Alzheimer's Disease with dementia is treated by injection of a TNF antagonist selected from the group of etanercept, infliximab, CDP 870, D2E7, or onercept in a therapeutically effective dose to the anatomic area adjacent to the spine, with the dose repeated as a form of chronic therapy at intervals as often as twice per week to as little as once per three months.

In one preferred embodiment a patient with post-herpetic neuralgia complaining of severe persistent pain is treated by injection of a TNF antagonist selected from the group of etanercept, infliximab, CDP 870, D2E7, or onercept in a therapeutically effective dose to the anatomic area adjacent to the spine with a single dose administered 48 hours after beginning a course of antiviral medication.

In another preferred embodiment a patient with clinical depression is treated by intranasal administration of a TNF antagonist selected from the group of etanercept, infliximab, CDP 870, D2E7, or onercept in a therapeutically effective dose.

In another preferred embodiment a patient with lumbar radiculopathy due to an intervertebral disc herniation is treated by injection of a IL-1 antagonist selected from the group of IL-1 RA, Kineret, IL-1 R type 2 or IL-1 Trap in a therapeutically effective dose to the anatomic area adjacent to the involved disc.

In another preferred embodiment injection of the therapeutic molecule to the anatomic area adjacent to the spine is accomplished by interspinous injection.

In another preferred embodiment interspinous injection is accomplished by injection through the skin in the anatomic area between two adjacent spinous processes of the vertebral column.

An example of one preferred embodiment for treatment of lumbar radiculopathy due to disc herniation at the L3–4 interspace is the perispinal administration of etanercept 25 mg by injecting through the skin of the back, between the L3 and L4 spinous processes, to deliver etanercept in anatomic proximity to the site of disc herniation.

In another preferred embodiment injection of the therapeutic molecule to the anatomic area adjacent to the disc herniation is accomplished by subcutaneous injection.

In another preferred embodiment injection of the therapeutic molecule to the anatomic area adjacent to the disc herniation is accomplished by epidural injection.

In another preferred embodiment injection of the therapeutic molecule to the anatomic area adjacent to the disc herniation is accomplished by peridural injection.

In another preferred embodiment injection of the therapeutic molecule to the anatomic area adjacent to the disc herniation is accomplished by perispinal injection.

Scientific Background:

Antibodies (immunoglobulins) are proteins produced by one class of lymphocytes (B cells) in response to specific exogenous foreign molecules (antigens). Monoclonal antibodies (mAB), identical immunoglobulin copies which recognize a single antigen, are derived from clones (identical copies) of a single B cell. This technology enables large quantities of an immunoglobulin with a specific target to be mass produced.

Monoclonal antibodies with a high affinity for a specific cytokine will tend to reduce the biologic activity of that cytokine. Substances which reduce the biologic effect of a cytokine can be described in any of the following ways: as a cytokine blocker; as a cytokine inhibitor; or as a cytokine antagonist. In this patent, the terms blocker, inhibitor, and antagonist are used interchangeably with respect to cytokines.

Advances in biotechnology have resulted in improved molecules as compared to simply using monoclonal antibodies. One such molecule is CDP 870 which, rather than being a monoclonal antibody, is a new type of molecule, that being an antibody fragment. By removing part of the antibody structure, the function of this molecule is changed so that it acts differently in the human body. Another new type of molecule, distinct from monoclonal antibodies and soluble receptors, is a fusion protein. One such example is etanercept. This molecule has a distinct function which acts differently in the human body than a simple soluble receptor or receptors.

Monoclonal antibodies, fusion proteins, and all of the specific molecules discussed above under the categories of TNF antagonists and interleukin antagonists are considered biologics, in contrast to drugs that are chemically synthesized. These biologics are derived from living sources (such as mammals (including humans), other animals, and microorganisms). The biologics mentioned above are manufactured using biotechnology, which usually involves the use of recombinant DNA technology. Cytokine antagonists are one type of biologic. Biologics are regulated through a specific division of the FDA.

Cytokine antagonists can take several forms. They may be monoclonal antibodies (defined above). They may be a monoclonal antibody fragment. They may take the form of a soluble receptor to that cytokine. Soluble receptors freely circulate in the body. When they encounter their target cytokine they bind to it, effectively inactivating the cytokine, since the cytokine is then no longer able to bind with its biologic target in the body. An even more potent antagonist consists of two soluble receptors fused together to a specific portion of an immunoglobulin molecule (Fe fragment). This produces a dimer composed of two soluble receptors which have a high affinity for the target, and a prolonged half-life. This new molecule is called a fusion protein. An example of this new type of molecule, called a fusion protein, is etanercept (Enbrel).

Tumor necrosis factor (TNF), a naturally occurring cytokine present in humans and other mammals, plays a key role in the inflammatory response, in the immune response and in the response to infection. TNF is formed by the cleavage of a precursor transmembrane protein, forming soluble molecules which aggregate in vivo to form trimolecular complexes. These complexes then bind to receptors found on a variety of cells. Binding produces an array of pro-inflammatory effects, including release of other pro-inflammatory cytokines, including IL-6, IL-8, and IL-1; release of matrix metalloproteinases; and up regulation of the expression of endothelial adhesion molecules, further amplifying the inflammatory and immune cascade by attracting leukocytes into extravascular tissues.

Interleukin-1 is a naturally occurring cytokine, present in humans and other mammals. Interleukin-1 plays a key role in the inflammatory response and in the immune response. Interleukin-1 receptor antagonist (IL-1 RA) is a naturally occurring molecule which reduces the biologic effects of interleukin-1 by interfering with the binding of IL-1 to its receptor (IL-1 R1, interleukin-1 type 1 receptor). Kineret (Amgen) is a recombinant form of IL-1 RA which is FDA approved for treating rheumatoid arthritis. IL-1 Receptor Type 2 (Amgen), AMG719 (Amgen), and IL-1 Trap (Regeneron), are all biologic inhibitors of interleukin-1.

Etanercept (Enbrel®, Amgen), infliximab (Remicade®), D2E7, CDP 870, and onercept are potent and selective inhibitors of TNF. D2E7, CDP 870, and onercept are in clinical development. Etanercept and infliximab are FDA approved for chronic systemic use to treat rheumatoid arthritis.

Perispinal administration and intranasal administration of cytokine antagonists are new methods of administration of the specific cytokine antagonists of consideration here. These new methods result in improved delivery of these therapeutic molecules to the nervous system, either by local diffusion; by improved transport into the cerebrospinal fluid (CSF); or by direct transport into the CNS. Improved delivery thereby enables these specific cytokine antagonists to produce therapeutic benefit for patients with a variety of neurological and neuropsychiatric disorders.

Clinical Disorders

Patients with the following clinical disorders, among others, will benefit from treatment with cytokine antagonists delivered by the perispinal route or by intranasal administration:

1. Unipolar and Bipolar Affective Disorders

These are disorders of mood, causing recurrent depression and/or recurrent episodes of mood elevation, resulting in mania or hypomania. Current treatment regimens include the use of lithium carbonate, carbamazepine, or antipsychotic medication. Inflammatory cytokines are involved in the regulation of sleep and mood. In the present invention, perispinal administration of TNF antagonists or IL-1 antagonists is used for the acute or chronic treatment of these disorders. Clinical experience has demonstrated the rapid beneficial effect, and the lasting beneficial effect, of this method of treatment for these disorders. Acute administration of a TNF antagonist results in rapid improvement in affect and cognitive function. Chronic administration results in decreased lability of mood, increased time intervals between mood swings, and decreased amplitude of mood swings. Chronic administration may require twice weekly dosing, but in some patients will be effective when given much less often, sometimes as little as once per three months. Some patients may only require a single dose given at the onset of a mood disturbance. Sleep improvement and improvement in cognition is noted by patients responding to treatment.

2. Schizoaffective Illness

These patients have a thought disorder as well as a mood disorder. These patients can be difficult to distinguish from patients with pure schizophrenia or bipolar affective disorder. Most require treatment with anti-psychotic medication. Some will respond to treatment with lithium carbonate. These patients respond to treatment with the cytokine antagonists of consideration here delivered by the perispinal route. Treatment can be acute or chronic, as outlined in the discussion of unipolar and bipolar affective disorder.

3. Schizophrenia

Schizophrenia is a thought disorder prevalent throughout the world, affecting about 1% of the world's population. Paranoid schizophrenia is a common clinical type. Treatment is almost uniformly unsuccessful. Chronic treatment with neuroleptic medication is usually required with less than satisfactory results These patients have a disturbance in cytokine patterns, which is amenable to treatment with TNF or IL-1 antagonists by perispinal administration or by intranasal administration. Treatment can be acute or chronic, as outlined in the discussion of unipolar and bipolar affective disorder.

4. Depression

Clinical depression is characterized by depressed mood, often accompanied by additional clinical manifestations, such as sleep disturbance, weight loss, loss of appetite, apathy, anhedonia, and when severe, can be associated with suicidal ideation. It is currently treated, when indicated, with antidepressant medication, most commonly selective serotonin reuptake inhibitors (SSRIs) or tricyclic antidepressants. Post-partum depression can be especially serious, occuring after childbirth. Depression, even when treated, is associated with an increased suicide risk. These patients have a disturbance in cytokine patterns, which is amenable to treatment with TNF or IL-1 antagonists by perispinal administration or by intranasal administration. Clinical experience has demonstrated the rapid beneficial effect, and the lasting beneficial effect, of this method of treatment for these disorders. Treatment can be acute or chronic, as outlined in the discussion of unipolar and bipolar affective disorder.

5. Autism

This is an incapacitating, lifelong cognitive developmental disability which usually appears in early childhood. There is no reasonably effective treatment regimen. These patients have a disturbance in cytokine patterns, which is amenable to treatment with TNF or IL-1 antagonists by perispinal administration or by intranasal administration.

6. Anorexia Nervosa

Anorexia Nervosa is an eating disorder characterized by refusal to maintain body weight above a minimally normal weight (usually defined as 85% of expected), combined with a disturbance in the way one's weight or body shape is experienced and intense fear of gaining weight. This is associated with a disturbance in cytokine patterns, which is amenable to treatment with TNF or IL-1 antagonists by perispinal administration or by intranasal administration. Clinical experience has demonstrated weight gain as a result of the use of TNF antagonists.

7. Obsessive-Compulsive Disorder (OCD) OCD is an anxiety disorder characterized by persistent intrusive thoughts that can only be alleviated by patterns of rigid and ceremonial behavior. Traditional treatment may include the use of SSRIs but is often unsuccessful. These patients have a disturbance in cytokine patterns, which is amenable to treatment with TNF or IL-1 antagonists by perispinal administration or by intranasal administration.

8. Narcotic Addiction

People attempting to discontinue the use of narcotics have great difficulty without pharmacologic assistance if they have been using the narcotics chronically at high dosage levels. Chrnoic narcotic use creates significant physiological changes in the CNS. These patients have a disturbance in cytokine patterns, which is amenable to treatment with TNF or IL-1 antagonists by perispinal administration or by intranasal administration.

9. Alcohol Withdrawl

People attempting to discontinue the use of alcohol have great difficulty without pharmacologic assistance if they have been consuming large amounts of alcohol on a chronic basis. Both chrnoic alcohol use and alcohol withdrawl create significant physiological changes in the CNS. These patients have a disturbance in cytokine patterns, which is amenable to treatment with TNF or IL-1 antagonists by perispinal administration or by intranasal administration.

10. Smoking Cessation/Nicotine Withdrawal

People attempting to stop smoking tobacco have great difficulty without pharmacologic assistance. Tobacco smoke contains nicotine, which, on a chronic basis, has potent biologic effects. Smoking cessation and the accompanying nicotine withdrawal creates significant physiological changes in the CNS. These patients have a disturbance in cytokine patterns, which is amenable to treatment with TNF or IL-1 antagonists by perispinal administration or by intranasal administration.

11. Degenerative Disorders, Including Parkinson's Disease, Alzheimer's Disease, Idiopathic Dementia and ALS These chronic neurological disorders include but are not limited to Alzheimer's Disease, Pick's Disease, Creutzfeldt-Jacob Disease (CJD), Variant CJD, Parkinson's Disease, Lewy Body Disease, Idiopathic Dementia, Amyotrophic Lateral Sclerosis (ALS), and the Muscular Dystrophies. Alzheimer's Disease, Pick's Disease, CJD, Lewy Body Disease, Idiopathic Dementia and Variant CJD are all irreversible, progressive forms of dementia. ALS is a progressive motor neuron disease of unknown etiology characterized by progressive weakness. The muscular dystrophies are a group of related neuromuscular disorders which result in progressive loss of muscular function. The exact causation of all of these disorders is uncertain, and there are no curative treatment regimens currently available. Many of these disorders involve CNS, neuronal, or muscular inflammation, and many also involve accelerated neuronal apoptosis. Treatment of these disorders with TNF antagonists or IL-1 antagonists by perispinal administration and/or intranasal administration leads to clinical improvement and/or slowing of disease progression. Chronic treatment regimens are necessary, with doses usually administered at an interval varying from twice per week to once per month. Clinical experience has demonstrated the beneficial effect of this method of treatment for these disorders.

12. Spinal Cord Injury

About 10,000 cases occur per year in the U.S., with a current population of over 200,000 patients with residual neurologic damage, many of whom are paralyzed (quadriplegia or paraplegia). Current treatment for the acute injury is inadequate. In the early 1990's it was shown that early (within 8 hours of injury) treatment with high doses of steroids (methyl prednisolone) was beneficial for some of these patients. Surgical stabilization and spinal decompression is often necessary because of excessive swelling (edema) which can itself cause further severe injury to the cord due to further compression of the cord against its bony spinal canal. The etiology of most of these cases are motor vehicle accidents, with the remainder being sports injuries, falls, and other accidents. The window of opportunity for treatment is small, since massive swelling can occur within minutes. The use of a cytokine antagonist, delivered by perispinal administration, ameliorates neurological damage caused by acute spinal cord injury, and is also beneficial for patients with chronic spinal cord injury. Treatment with TNF antagonists or IL-1 antagonists given parenterally by perispinal administration leads to clinical improvement. Clinical experience has demonstrated the beneficial effect of this method of treatment for these disorders.

13. Headache Syndromes, Including Migraine Headaches and Cluster Headaches

Elevated levels of inflammatory cytokines are found in patients with severe neurologic headache syndromes, including, but not limited to migraine headaches and cluster headaches. Migraine headaches, a form of vascular headache, are common, and may have associated neurologic symptoms, such as visual disturbance, photophobia, and, in rare instances, can be associated with stroke. Treatment of these disorders with TNF antagonists or IL-1 antagonists by perispinal administration leads to clinical improvement. Treatment regimens can be either acute or chronic, and will vary with the clinical setting. Clinical experience has demonstrated the beneficial effect of this method of treatment for these disorders, often with rapid diminution of headache pain demonstrated.

14. Neuropathic Pain

TNF has been found to be of central importance in the pathogenesis of several types of neuropathic pain, including, but not limited to spinal radiculopathy, nerve root inflammation due to intervertebral disc herniation, and neuropathy associated with chronic constriction injury. There are many other forms of neuropathic pain, defined generally as pain initiated or caused by a primary lesion or dysfunction in the nervous system. Treatment of these disorders with TNF antagonists or IL-1 antagonists by perispinal administration leads to clinical improvement. Treatment regimens can be either acute or chronic, and will vary with the clinical setting. Clinical experience has demonstrated the beneficial effect of this method of treatment for several different forms of neuropathic pain.

15. Lumbar And Cervical Radiculopathy

Inflammation of the nerve roots in the lumbar or cervical region may lead to neurologic dysfunction. These forms of radiculopathy commonly result in pain in a nerve root distribution, often with sensory dysfunction characterized by numbness and/or paresthesia. A smaller subset of these patients also experience motor weakness. TNF has been strongly implicated in the pathogenesis of these clinical syndromes. Release of TNF from damaged intervertebral discs, as the result of disc herniation or other forms of disc disease has been suggested to be the central causative factor. Clinical experience has established the efficacy of treatment of these disorders with TNF antagonists delivered by perispinal administration.

16. Fibromyalgia

Fibromyalgia is a syndrome of unknown cause that results in chronic, widespread neuromuscular pain and fatigue, often with multiple, tender areas, sleep disturbance, and additional clinical symptoms. Clinical experience has established the efficacy of treatment of patients with this diagnosis utilizing TNF antagonists delivered by perispinal administration. Treatment with TNF antagonists or IL-1 antagonists given parenterally by perispinal administration leads to clinical improvement.

17. Low Back Pain

Low back pain (LBP) can result from a wide variety of clinical conditions. Many forms of LBP are mild or spontaneously resolve. Other types are severe, treatment refractory, and can either be acute, subacute or chronic. Many of these patients have been diagnosed with intervertebral disc disease, ranging from a solitary annular tear of one disc capsule, to a mild disc bulge, to multiple large disc herniations present in a single individual. Clinical experience has established the efficacy of treatment of patients with these disc disorders through the use of TNF antagonists delivered by perispinal administration. In addition this method of treatment has been beneficial for other patients with back pain, including those patients with apparently normal MRI examination of the spine. Many of these patients may have undiagnosed annular tears of their intervertebral disc capsules, or other forms of internal disc derangement. Treatment with TNF antagonists or IL-1 antagonists given parenterally by perispinal administration leads to clinical improvement.

18. Post-Herpetic Neuralgia

Persistent severe pain following herpes zoster can be chronic and treatment refractory, particularly with patients over the age of 65. Inflammation in the dorsal root ganglion, continuing after the healing of cutaneous lesions, has been documented. Treatment with TNF antagonists, administered by the perispinal route, in conjunction with orally administered anti-viral therapy, such as famciclovir, helps alleviate this form of neuropathic pain. Treatment with TNF antagonists or IL-1 antagonists given parenterally by perispinal administration leads to clinical improvement. Clinical experience has confirmed the beneficial effect of this treatment modality.

19. Vertebral Disc Disease

Disease of one or more intervertebral discs can be the result of trauma, aging, arthritis, or other inflammatory disorders. The resulting damage can produce disruption of the capsule of the disc, allowing release of TNF into the extradiscal space. This may result in TNF-mediated neurotoxicity, inflammation, and resulting neuropathic pain and/or sensory and motor neuropathy or radiculopathy. These patients may have frank disc herniation, or more subtle forms of disc disruption, such as disc bulging, disc protrusion, or annular tear of the disc capsule. Many of these patients are diagnosed as having degenerative disc disease. Treatment with TNF antagonists or IL-1 antagonists given parenterally by perispinal administration leads to clinical improvement. Extensive clinical experience has documented the favorable effect of this method of treatment for patients in this clinical category.

20. Chronic Fatigue Syndrome (CFS)

Patients with CFS have severe chronic fatigue of six months or longer duration, with known causes excluded; and have additional symptoms, including memory impairment, sore throat, adenopathy, myalgias, arthralgias, and sleep disturbance. Treatment with TNF antagonists or IL-1 antagonists by perispinal administration or intranasal administration leads to clinical improvement. Clinical experience has documented the favorable effect of this method of treatment for patients with this diagnosis.

21. Reflex Sympathetic Dystrophy (RSD)

RSD is a chronic pain syndrome characterized by chronic, severe, treatment refractory neuropathic pain of unknown etiology, but often associated with a pre-existing injury, and often accompanied by skin and joint changes and diminished motor function in the involved extremity. Inflammatory cytokines are involved in the pathophysiology. Treatment with TNF antagonists or IL-1 antagonists given parenterally by perispinal administration leads to clinical improvement.

Dosages and Routes of Administration

The dosage of a cytokine antagonist used for perispinal administration will in general be within one order of magnitude of the dosage used as a single dose for systemic administration. For example, if the usual dose when administered systemically is 100 mg, then the dose used for perispinal administration will usually be between 10mg and 100 mg. The exception to this general guideline occurs with intrathecal injections or intranasal administration, where the required dosage is smaller, usually in the range of 1% to 10% of the corresponding systemic dose for the intrathecal route, and usually in the range of 10% to 25% for the intranasal route.

For the treatment of acute or severe conditions, the dose will generally be adjusted upward. In the above example the dose selected would therefore be 100 mg, rather than 10 mg, if the condition were acute and/or severe.

Localized perilesional injection can allow the use of subcutaneous administration even in the case when the medication is normally administered intravenously. An example of this would be the use of infliximab subcutaneously in the interspinous area for the treatment of nerve root inflammation associated with intervertebral disc disease.

For treating the above diseases with the above mentioned TNF antagonists, these TNF antagonists may be administered by the following routes:

The above TNF antagonists may be administered subcutaneously in the human and the dosage level is in the range of 1 mg to 300 mg per dose, with dosage intervals as short as one day.

The above TNF antagonists may be administered intramuscularly in the human and the dosage level is in the range of 1 mg to 200 mg per dose, with dosage intervals as short as two days.

The above TNF antagonists may be administered epidurally in the human and the dosage level is in the range of 1 mg to 300 mg per dose, with dosage intervals as short as two days.

The above TNF antagonists may be administered peridurally in the human and the dosage level is in the range of 1 mg to 300 mg per dose, with dosage intervals as short as two days.

The above TNF antagonists may be administered by interspinous injection in the human and the dosage level is in the range of 1 mg to 300 mg per dose, with dosage intervals as short as two days.

The above TNF antagonists may be administered by intranasal administration utilizing a nasal spray or nasal inhaler in the human and the dosage level is in the range of 1 mg to 50 mg per dose, with dosage intervals as short as four hours.

Interleukin-1 antagonists are administered in a therapeutically effective dose, which will generally be 10 mg to 200 mg per dose. The dosage interval will be as short as once daily.

ADVANTAGES OF THE PRESENT INVENTION

Accordingly, an advantage of the present invention is that it provides for the localized administration of specific biologics as a new pharmacologic treatment of neurological and neuropsychiatric diseases and disorders; such that the use of these cytokine antagonists will result in the amelioration of these conditions.

Another advantage of the present invention is that it provides for specific biologics delivered by anatomically localized administration, which, when compared to systemic administration, produces one or more of the following: greater efficacy; more rapid onset; longer duration of action; improved delivery to the CNS; or fewer side effects.

Another advantage of the present invention is that it provides for specific biologics for providing suppression and inhibition of the action of cytokines in a human to treat neurological and neuropsychiatric diseases and disorders.

Another advantage of the present invention is that it provides for specific biologics administered by specific methods for treating humans with neurological and neuropsychiatric diseases and disorders which due to their biologic action will produce clinical improvement in the patient and will give the patient a better opportunity to heal, slow disease progression, prevent neurological damage, reduce pain, or otherwise improves the patient's health.

Another advantage of the present invention is that it provides for specific biologics, including cytokine antagonists to tumor necrosis factor alpha or to interleukin-1, using localized administration, including perispinal administration, as the preferred form of administration, for the treatment of neurological disorders, including dementia, low back pain, and neuropathic pain.

Another advantage of the present invention is that it provides for specific biologics, including cytokine antagonists to tumor necrosis factor alpha or to interleukin-1, using localized administration, including perispinal administration or intranasal administration, as the preferred form of delivery, for the treatment of neuropsychiatric disorders, including depression, schizophrenia, anorexia nervosa and chronic fatigue syndrome.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A method for treating TNF mediated dementias, being Alzheimer's Disease, Pick's Disease, Lewy Body Disease and Idiopathic Dementia, in a human by inhibiting the action of tumor necrosis factor (TNF) through the administration of a TNF antagonist comprising the steps of:
    a) administering a therapeutically effective dosage level to said human of said TNF antagonist selected from the group consisting of etanercept, soluble TNF receptor Type I, pegylated soluble TNF receptor Type I (PEGs TNF-R1) and onercept, a recombinant TNF binding protein (r-TBP-1) (Serono); and
    b) administering said dose parenterally by perispinal administration into the perispinal space without direct intrathecal injection.

2. A method for treating in accordance with claim 1, wherein the step of administering said TNF antagonist is performed through any of the following routes: subcutaneous, intramuscular, interspinous, parenteral, or epidural.

3. A method for treating spinal cord injury in a human by inhibiting the action of tumor necrosis factor (TNF) through the administration of a TNF antagonist comprising the steps of:
 a) administering a therapeutically effective dosage level to said human of said TNF antagonist selected from the group consisting of etanercept, soluble TNF receptor Type I, pegylated soluble TNF receptor Type I (PEGS TNF-R1) and onercept, a recombinant TNF binding protein (r-TBP-1) (Serono); and
 b) administering said dose parenterally by perispinal administration into the perispinal space without direct intrathecal injection.

4. A method for treating TNF mediated pain syndromes, being Migraine Headaches, Cluster Headaches, Neuropathic Pain, Fibromyalgia, Post-Herpetic Neuralgia and Reflex Sympathetic Dystrophy (RSD) in a human by inhibiting the action of tumor necrosis factor (TNF) through the administration of a TNF antagonist comprising the steps of:
 a) administering a therapeutically effective dosage level to said human of said TNF antagonist selected from the group consisting of etanercept, soluble TNF receptor Type I, pegylated soluble TNF receptor Type I (PEGs TNF-R1) and onercept, a recombinant TNF binding protein (r-TBP-1) (Serono); and
 b) administering said dose parenterally by perispinal administration into the perispinal space without direct intrathecal injection.

5. A method for treating TNF mediated back pain syndromes being Lumbar and Cervical Radiculopathy, Low Back Pain and Vertebral Disc Disease in a human by inhibiting the action of tumor necrosis factor (TNF) through the administration of a TNF antagonist comprising the steps of:
 a) administering a therapeutically effective dosage level to said human of said TNF antagonist selected from the group consisting of etanercept, soluble TNF receptor Type I, pegylated soluble TNF receptor Type I (PEGs TNF-R1) and onercept, a recombinant TNF binding protein (r-TBP-1) (Serono); and
 b) administering said dose parenterally by perispinal administration into the perispinal space without direct intrathecal injection.

6. A method for treating Alzheimer's Disease in a human by inhibiting the action of tumor necrosis factor (TNF) through the administration of a TNF antagonist comprising the steps of:
 a) administering a therapeutically effective dosage level to said human of said TNF antagonist selected from the group consisting of etanercept, and onercept, a recombinant TNF binding protein (r-TBP-1) (Serono); and
 b) administering said dose parenterally by perispinal administration into the perispinal space without direct intrathecal injection using the interspinous route.

7. A method for treating low back pain in a human by inhibiting the action of tumor necrosis factor (TNF) through the administration of a TNF antagonist comprising the steps of:
 a) administering a therapeutically effective dosage level to said human of said TNF antagonist selected from the group consisting, of etanercept, and onercept, a recombinant TNF binding protein (r-TBP-1) (Serono); and
 b) administering said dose parenterally by perispinal administration into the perispinal space without direct intrathecal injection using the interspinous route.

8. A method for treating fibromyalgia in a human by inhibiting the action of tumor necrosis factor (TNF) through the administration of a TNF antagonist comprising the steps of:
 a) administering a therepeutically effective dosage level to said human of said TNF antagonist selected from the group consisting of etanercept, and onercept, a recombinant TNF binding protein (r-TBP-1) (Serono); and
 b) administering said dose parenterally by perispinal administration into the perispinal space without direct intrathecal injection using the interspinous route.

9. A method for treating vertebral disc disease in a human by inhibiting the action of tumor necrosis factor (TNF) through the administration of a TNF antagonist comprising the steps of:
 a) administering a therapeutically effective dosage level to said human of said TNF antagonist selected from the group consisting of etanercept, and onercept, a recombinant TNF binding protein (r-TBP-1) (Serono); and
 b) administering said dose parenterally by perispinal administration into the perispinal space without direct intrathecal injection using the interspinous route.

10. A method for treating nerve root inflammation in a human by inhibiting the action of tumor necrosis factor (TNF) through the administration of a TNF antagonist comprising the steps of:
 a) administering a therapeutically effective dosage level to said human of said TNF antagonist selected from the group consisting of etanercept, and onercept, a recombinant TNF binding protein (r-TBP-1) (Serono); and
 b) administering said dose parenterally by perispinal administration into the perispinal space without direct intrathecal injection.

11. A method for treating nerve root inflammation in a human by inhibiting the action of tumor necrosis factor (TNF) through the administration of a TNF antagonist comprising the steps of:
 a) administering a therapeutically effective dosage level to said human of said TNF antagonist selected from the group consisting of etanercept, infliximab, CDP 870 (a humanized monoclonal anti-TNF-alpha antibody fragment). D2E7 (a human anti-TNF mAb), soluble TNF receptor Type I, pegylated soluble TNF receptor Type I (PEGs TNF-R1) and onercept, a recombinant TNF binding protein (r-TBP-1) (Serono); and
 b) administering said dose parenterally by perispinal administration into the perispinal space without direct intrathecal injection using the interspinous route.

12. A method for treating migraine headache in a human by inhibiting the action of tumor necrosis factor (TNF) through the administration of a TNF antagonist comprising the steps of:
 a) administering a therapeutically effective dosage level to said human of said TNF antagonist selected from the group consisting of etanercept, and onercept, a recombinant TNF binding protein (r-TBP-1) (Serono); and
 b) administering said dose parenterally by perispinal administration into the perispinal space without direct intrathecal injection using the interspinous route.

13. A method for treating low back pain in a human by inhibiting the action of tumor necrosis factor (TNF) through the administration of a TNF antagonist comprising the steps of:
 a) administering a therapeutically effective dosage level to said human of said TNF antagonist; selected from tho group consisting of soluble TNF receptor Type I and pegylated soluble TNF receptor Type I; and b) administering said dose parenterally by perispinal administration into the perispinal space without direct intrathecal injection using the interspinous route.

14. A method for treating in accordance with claim 5, wherein the step of administering said TNF antagonist is performed through any of the following routes: subcutaneous, intramuscular, interspinous, parenteral, or epidural.

15. A method for treating Neuropathic Pain in a human by inhibiting the action of tumor necrosis factor (TNF) through the administration of a TNF antagonist comprising the steps of:
  a) administering a therapeutically effective dosage level to said human of said TNF antagonist selected from the group consisting of etanercept, and onercept, a recombinant TNF binding protein (r-TBP-1) Serono); and
  b) administering said dose parenterally by perispinal administration into the perispinal space without direct intrathecal injection using the interspinous route.

* * * * *

UNITED STATES PATENT AND TRADEMARK OFFICE
CERTIFICATE OF CORRECTION

PATENT NO. : 6,982,089 B2
DATED : January 3, 2006
INVENTOR(S) : Dr. Edward L. Tobinick It is certified that error appears in the above-identified patent and that said Letters Patent is hereby corrected as shown below:

<u>Column 15,</u>
Line 43, should read:
6. A method for treating Alzheimer's Disease in a human by inhibiting the action of tumor necrosis factor (THF) through the administration of a TNF antagonist comprising the steps of:
   a) administering a therapeutically effective dosage level to said human of said TNF antagonist selected from the group consisting of etanercept, CDP 870, and onercept, a recombinant TNF binding protein (r-TBP-1) (Serono); and
   b) administering said dose parenterally by perispinal administration into the perispinal space without direct intrathecal injection using the interspinous route.

Signed and Sealed this

Eleventh Day of April, 2006

JON W. DUDAS
*Director of the United States Patent and Trademark Office*

UNITED STATES PATENT AND TRADEMARK OFFICE
CERTIFICATE OF CORRECTION

PATENT NO. : 6,982,089 B2  Page 1 of 1
APPLICATION NO. : 10/269745
DATED : January 3, 2006
INVENTOR(S) : Dr. Edward L. Tobinick It is certified that error appears in the above-identified patent and that said Letters Patent is hereby corrected as shown below:

Column 15,
Line 43, should read:
6. A method for treating Alzheimer's Disease in a human by inhibiting the action of tumor necrosis factor (TNF) through the administration of a TNF antagonist comprising the steps of:
   a) administering a therapeutically effective dosage level to said human of said TNF antagonist selected from the group consisting of etanercept, CDP 870, and onercept, a recombinant TNF binding protein (r-TBP-1) (Serono); and
   b) administering said dose parenterally by perispinal administration into the perispinal space without direct intrathecal injection using the interspinous route.

This certificate supersedes the Certificate of Correction issued April 11, 2006.

Signed and Sealed this

Twenty-ninth Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 6,982,089 B2  Page 1 of 2
APPLICATION NO. : 10/269745
DATED : January 3, 2006
INVENTOR(S) : Edward L. Tobinick It is certified that error appears in the above-identified patent and that said Letters Patent is hereby corrected as shown below:

On the title page of the patent, please delete the following paragraph:

"Continuation-in-part of application No. 10/236,097, filed on Sep. 6, 2002, now abandoned, which is a continuation-in-part of application No. 09/841,844, filed on Apr. 25, 2001, now Pat. No. 6,537,549, which is a continuation-in-part of application No. 09/826,976, filed on Apr. 5, 2001, now Pat. No. 6,419,944, which is a continuation-in-part of application No. 09/563,651, filed on May 2, 2000, now Pat. No. 6,471,961, which is a continuation-in-part of application No. 09/476,643, filed on Dec. 31, 1999, now Pat No. 6,177,077, which is a continuation-in-part of application No. 09/275,070, filed on March 23, 1999, now Pat No. 6,015,557, which is a continuation-in-part of application No. 09/256,388, filed on Feb. 24, 1999, now abandoned."

and insert therefore:

-- This is a continuation-in-part of application Ser. No. 10/236,097, filed on Sep. 6, 2002 now abandoned, which is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/563,651, filed on May 2, 2000, now U.S. Pat. No. 6,471,961, and a continuation-in-part of application 09/666,068, filed on December 11, 2000, now U.S. Pat No. 6,379,666, which is a divisional of application Ser. No. 09/476,643, filed Dec. 31, 1999, now U.S. Pat. No. 6,177,077, which is a continuation-in-part of Serial No. 09/275,070, filed March 23, 1999, now U.S. Pat. No. 6,015,557, which is a continuation-in-part of application Ser. No. 09/256,388, filed on Feb. 24, 1999, now abandoned. --

In column 1, lines 6 - 20, please delete the following paragraph:

"This is a continuation-in-part of application Ser. No. 10/236,097, filed on Sep. 6, 2002 now abandoned, which is a continuation-in-part of application Ser. No. 09/841,844, filed on Apr. 25, 2001Now U.S. Pat. No. 6,537,549, which is a continuation-in-part of application Ser. No. 09/826,976, filed on Apr. 5, 2001, now U.S. Pat. No. 6, 419,944, which is a continuation-in-part of application Ser. No. 09/563,651, filed on May 2, 2000, Now U.S. Pat. No. 6,471,961, Signed and Sealed this Twenty-seventh Day of July, 2010

David J. Kappos
*Director of the United States Patent and Trademark Office* continuation-in-part of application Ser. No. 09/476,643, filed Dec. 31, 1999, now U.S. Pat No. 6,177,077, which is a continuation-in-part of Serial No. 09/275,070, filed March 23, 1999, now U.S. Pat No. 6,015,557, which is a continuation-in-part of application Ser. No. 09/256,388, filed on Feb. 24, 1999, now abandoned."

and insert therefore:

-- This is a continuation-in-part of application Ser. No. 10/236,097, filed on Sep. 6, 2002 now abandoned, which is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/563,651, filed on May 2, 2000, now U.S. Pat. No. 6,471,961, and a continuation-in-part of application 09/666,068, filed on December 11, 2000, now U.S. Pat. No. 6,379,666, which is a divisional of application Ser. No. 09/476,643, filed Dec. 31, 1999, now U.S. Pat. No. 6,177,077, which is a continuation-in-part of Serial No. 09/275,070, filed March 23, 1999, now U.S. Pat. No. 6,015,557, which is a continuation-in-part of application Ser. No. 09/256,388, filed on Feb. 24, 1999, now abandoned. --

UNITED STATES PATENT AND TRADEMARK OFFICE
CERTIFICATE OF CORRECTION

| | | |
|---|---|---|
| PATENT NO. | : 6,982,089 B2 | Page 1 of 2 |
| APPLICATION NO. | : 10/269745 | |
| DATED | : January 3, 2006 | |
| INVENTOR(S) | : Tobinick | |

It is certified that error appears in the above-identified patent and that said Letters Patent is hereby corrected as shown below:

On the title page of the patent, please delete the following paragraph in item "(63)":

"This is a continuation-in-part of application Ser. No. 10/236,097, filed on Sep. 6, 2002 now abandoned, which is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/563,651, filed on May 2, 2000, now U.S. Pat. No. 6,471,961, and a continuation-in-part of application 09/666,068, filed on December 11, 2000, now U.S. Pat No. 6,379,666, which is a divisional of application Ser. No. 09/476,643, filed Dec, 31, 1999, now U.S. Pat. No. 6,177,077, which is a continuation-in-part of Serial No. 09/275,070, filed March 23, 1999, now U.S. Pat. No. 6,015,557, which is a continuation-in-part of application Ser. No. 09/256,388, filed on Feb. 24, 1999, now abandoned."

and insert therefore:

-- Continuation-in-part of application No. 10/236,097, filed on Sep. 6, 2002, now abandoned, which is a continuation-in-part of application No. 09/841,844, filed on Apr. 25, 2001, now U.S. Pat. No. 6,537,549, which is a continuation-in-part of application No. 09/826,976, filed on Apr. 5, 2001, now U.S. Pat. No. 6,419,944, which is a continuation-in-part of application No. 09/563,651, filed on May 2, 2000, now U.S. Pat. No. 6,471,961, and a continuation-in-part of application No. 09/666,068, filed on December 11, 2000, now U.S. Pat. No. 6,379,666, which is a divisional of application No. 09/476,643, filed Dec. 31, 1999, now U.S. Pat No. 6,177,077, which is a continuation-in-part of application No. 09/275,070, filed March 23, 1999, now U.S. Pat. No. 6,015,557, which is a continuation-in-part of application No. 09/256,388, filed on Feb. 24, 1999, now abandoned;
and application No. 10/269,745 is a continuation-in-part of application No. 09/841,844, filed on Apr. 25, 2001, now U.S. Pat. No. 6,537,549, which is a continuation-in-part of application No. 09/826,976, filed on Apr. 5, 2001, now U.S. Pat. No. 6,419,944, which is a continuation-in-part of application No. 09/563,651, filed on May 2, 2000, now U.S. Pat. No. 6,471,961; and application Ser. 09/826,976 is a continuation-in-part of application No. 09/666,068, filed on December 11, 2000, now Signed and Sealed this
Twenty-fifth Day of February, 2014

Michelle K. Lee
*Deputy Director of the United States Patent and Trademark Office*

CERTIFICATE OF CORRECTION (continued)
U.S. Pat. No. 6,982,089 B2

U.S. Pat. No. 6,379,666, which is a divisional of application No. 09/476,643, filed Dec. 31, 1999, now U.S. Pat. No. 6,177,077, which is a continuation-in-part of application No. 09/275,070, filed March 23, 1999, now U.S. Pat. No. 6,015,557, which is a continuation-in-part of application No. 09/256,388, filed on Feb. 24, 1999, now abandoned. --

In the Specification

In column 1, lines 6-20, please delete the following paragraph:

"This is a continuation-in-part of application Ser. No. 10/236,097, filed on Sep. 6, 2002 now abandoned, which is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/563,651, filed on May 2, 2000, now U.S. Pat. No. 6,471,961, and a continuation-in-part of application 09/666,068, filed on December 11, 2000, now U.S. Pat. No. 6,379,666, which is a divisional of application Ser. No. 09/476,643, filed Dec. 31, 1999, now U.S. Pat. No.6, 177,077, which is a continuation-in-part of Serial No. 091275,070, filed March 23, 1999, now U.S. Pat. No. 6,015,557, which is a continuation-in-part of application Ser. No. 091256,388, filed on Feb. 24, 1999, now abandoned."

and insert therefore:

-- This application Ser. No. 10/269,745 is a continuation-in-part of application Ser. No. 10/236,097, filed on Sep. 6, 2002, now abandoned, which is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/563,651, filed on May 2, 2000, now U.S. Pat. No. 6,471,961, and a continuation-in-part of application Ser. No. 09/666,068, filed on December 11, 2000, now U.S. Pat. No. 6,379,666, which is a divisional of application Ser. No. 09/476,643, filed Dec. 31, 1999, now U.S. Pat. No. 6,177,077, which is a continuation-in-part of application Ser. No. 09/275,070, filed March 23, 1999, now U.S. Pat. No. 6,015,557, which is a continuation-in-part of application Ser. No. 09/256,388, filed on Feb. 24, 1999, now abandoned; and application Ser. No. 10/269,745 is a continuation-in-part of application Ser. No. 09/841,844, filed on Apr. 25, 2001, now U.S. Pat. No. 6,537,549, which is a continuation-in-part of application Ser. No. 09/826,976, filed on Apr. 5, 2001, now U.S. Pat. No. 6,419,944, which is a continuation-in-part of application Ser. No. 09/563,651, filed on May 2, 2000, now U.S. Pat. No. 6,471,961; and application Ser. No. 09/826,976 is a continuation-in-part of application Ser. No. 09/666,068, filed on December 11, 2000, now U.S. Pat. No. 6,379,666, which is a divisional of application Ser. No. 09/476,643, filed Dec. 31, 1999, now U.S. Pat. No. 6,177,077, which is a continuation-in-part of application Ser. No. 09/275,070, filed March 23, 1999, now U.S. Pat. No. 6,015,557, which is a continuation-in-part of application Ser. No. 09/256,388, filed on Feb. 24, 1999, now abandoned. --